(12) United States Patent
Kidooka

(10) Patent No.: US 6,951,560 B1
(45) Date of Patent: Oct. 4, 2005

(54) BIPOLAR HIGH FREQUENCY TREATMENT TOOL FOR AN ENDOSCOPE

(75) Inventor: Satoshi Kidooka, Tokyo (JP)

(73) Assignee: PENTAX Corporation, Tokyo (JP)

( * ) Notice: Subject to any disclaimer, the term of this patent is extended or adjusted under 35 U.S.C. 154(b) by 149 days.

(21) Appl. No.: 10/404,557

(22) Filed: Apr. 2, 2003

(30) Foreign Application Priority Data

Apr. 9, 2002 (JP) .............................. 2002-106009

(51) Int. Cl.[7] .............................................. A61B 18/12

(52) U.S. Cl. ......................................... 606/51; 60/49

(58) Field of Search ............................. 606/49–52, 205

(56) References Cited

U.S. PATENT DOCUMENTS

| 5,171,258 A | 12/1992 | Bales et al. |
| 6,190,384 B1 | 2/2001 | Ouchi |
| 6,206,904 B1 | 3/2001 | Ouchi |
| 6,458,130 B1 * | 10/2002 | Frazier et al. ................ 606/51 |
| 2002/0123667 A1 | 9/2002 | Ouchi |

FOREIGN PATENT DOCUMENTS

| JP | 11155875 | 6/1999 |
| JP | 2000271128 | 10/2000 |
| JP | 2002253570 | 9/2002 |

OTHER PUBLICATIONS

English Language Abstract of 2002-271128.

* cited by examiner

*Primary Examiner*—Roy D. Gibson
*Assistant Examiner*—Aaron Roane
(74) *Attorney, Agent, or Firm*—Greenblum & Bernstein, P.L.C.

(57) ABSTRACT

A bipolar high frequency treatment tool has an insetting portion to be inserted into a body cavity through an endoscope. Two electrodes are pivotably supported within a slit formed to a supporting member attached to the distal end of the inserting portion. An insulating member is also located within the slit of the supporting member. The insulating block has substantially the same width as the slit. The insulating block has first and second side surfaces which are facing the first and second inner side surfaces of the slit, respectively, and deformed to define first and second spaces between the insulating block and the first and second inner side surfaces of the slit. The first and second electrodes are received in the first and second electrodes, respectively.

6 Claims, 7 Drawing Sheets

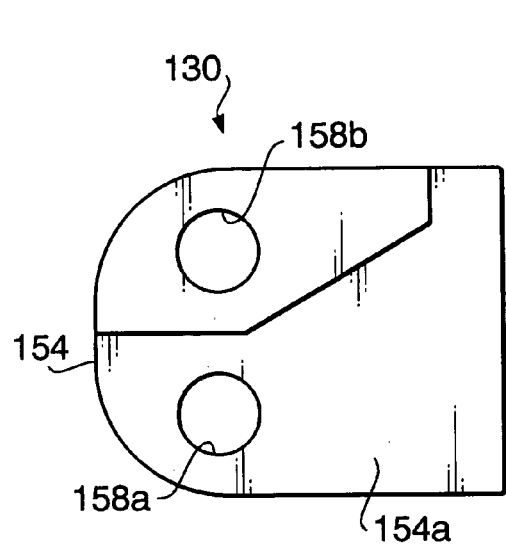 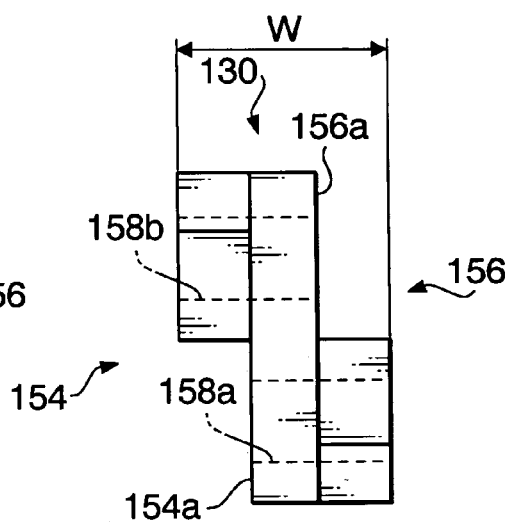
FIG.6A  FIG.6B
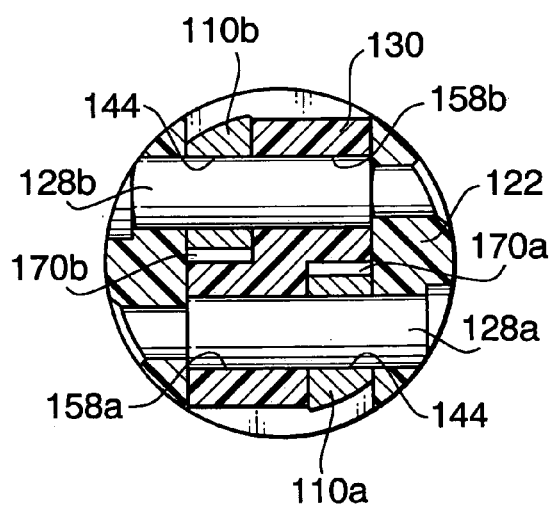
FIG. 7

US 6,951,560 B1

BIPOLAR HIGH FREQUENCY TREATMENT TOOL FOR AN ENDOSCOPE

BACKGROUND OF THE INVENTION

The present invention relates to a bipolar high frequency treatment tool having a pair of electrodes at the distal end of an inserting portion to be inserted into a body cavity through an endoscope.

A monopolar high frequency treatment tool is commonly used for endoscopic surgery. The monopolar high frequency treatment tool utilizes an electrode in combination with a counter plate attached to the body surface of a patient so that high frequency current flows between the electrode and the counter plate.

In the surgery utilizing the monopolar high frequency treatment tool, electric leak may occur if the patient comes in contact with a conductor other than the counter plate, which causes decrease of current effective to the operation and/or the surgeon to get burned.

Japanese patent provisional publication No. P2000-271128 discloses a bipolar high frequency treatment tool that overcomes the disadvantages of the monopolar high frequency treatment tool. The treatment tool disclosed in the above mentioned publication has a pair of electrodes mounted at the distal end of the treatment tool. The electrodes are arranged so as to open and close like pincers by a remote manipulation from the proximal end of the treatment tool. The electrodes are connected to the positive and negative terminals of a high frequency power supply, respectively, so that high frequency current flows through the tissue of the patient pinched between the electrodes.

The electrodes of the bipolar high frequency treatment tool have to be insulated from each other so that the high frequency current does not flow between the electrodes except the portions thereof that are expected to pinch the tissue of the patient. In order to achieve this, the electrodes disclosed in the above-mentioned publication are made of electrical insulating material such as plastic and ceramic with metal layers partially evaporated thereonto.

The electrodes, however, made of nonmetallic material are relatively low in strength and are easy to be broken. Further, the evaporated metal layer may come off from the electrode when, for example, it is rubbed against the inner wall of the channel of the endoscope through which the high bipolar frequency treatment tool is inserted into the body cavity.

For the forgoing reasons, there is a need for a bipolar high frequency treatment tool that has high strength while providing good insulation between the pair of electrodes.

SUMMARY OF THE INVENTION

The invention is advantageous in that a bipolar high frequency treatment tool and an electrode assembly that satisfy the above mentioned need are provided.

According to an aspect of the invention, there is provided a bipolar high frequency treatment tool having an inserting portion to be inserted into a body cavity through an endoscope. An electrode assembly is mounted to a distal end of the inserting portion. The electrode assembly includes a supporting member, first and second electrodes, and an insulating block.

The supporting member is attached to a distal end of the inserting portion. A slit is formed to the supporting member, which has first and second inner side surfaces facing to each other.

The first and second electrodes are held within the slit of the supporting member such that the electrodes are movable between open and closed positions and such that the front portions of the electrodes extend out from the slit. The front portions of the first and second electrodes become into contact with each other in the closed position and spaced apart form each other in the open position.

The insulating block has substantially the same width as the slit and located within the slit between the first and second electrodes. The insulating block has first and second side surfaces which face the first and second inner side surfaces of the slit, respectively. The first and second side surfaces are deformed to define first and second spaces between the insulating block and the first and second inner side surfaces of the slit for receiving the first and second electrodes, respectively.

In the bipolar high frequency treatment tool arranged as above, the first and second electrodes are well insulated from each other by the insulating block. Thus, the first and second electrodes are not required to be made of nonconductive materials but can be made of, for example, metal which has large mechanical strength.

It should be noted that the first and second spaces may have widths slightly larger than the widths of the first and second electrodes, respectively, so that the electrodes do not displace within the slit in the width direction thereof.

Optionally, the bipolar high frequency treatment tool further includes first and second pins held by the supporting member within the slit in parallel to and apart from each other, and the first and second electrodes are pivotably mounted to the first and second pins.

In the above case, the insulating block may have first and second through holes which extend substantially perpendicularly to the first and second side surfaces of the insulating block. The insulating block may be mounted to the supporting member by passing the first and second pins through the first and second through holes, respectively. The two pins passed through the insulating block prevent the insulating block from rotating within the slit of the supporting member. The insulating block supports the first and second pins and thereby prevents the pins from being bent and/or broken due to the force applied thereon as the first and second electrodes are moved between the open and closed positions.

Optionally, the insulating block may be formed integrally to the supporting member in the slit thereof to enhance the mechanical strength of the supporting member and, in turn, the mechanical strength of the electrode assembly.

BRIEF DESCRIPTION OF THE ACCOMPANYING DRAWINGS

FIG. 1 schematically shows a bipolar high frequency treatment tool according to an embodiment of the invention connected to a high frequency power supply;

Figure 1:
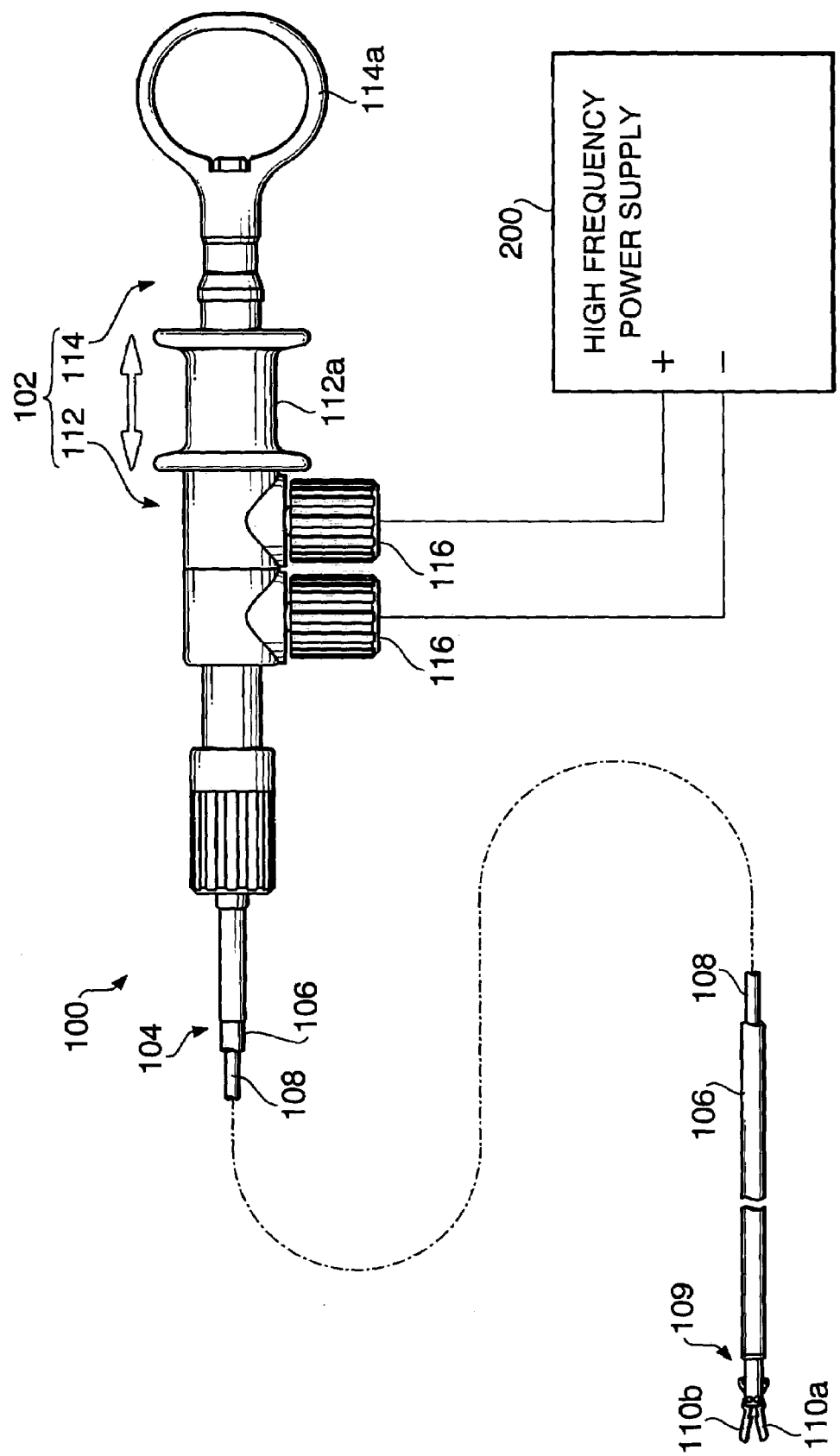
Figure 3:
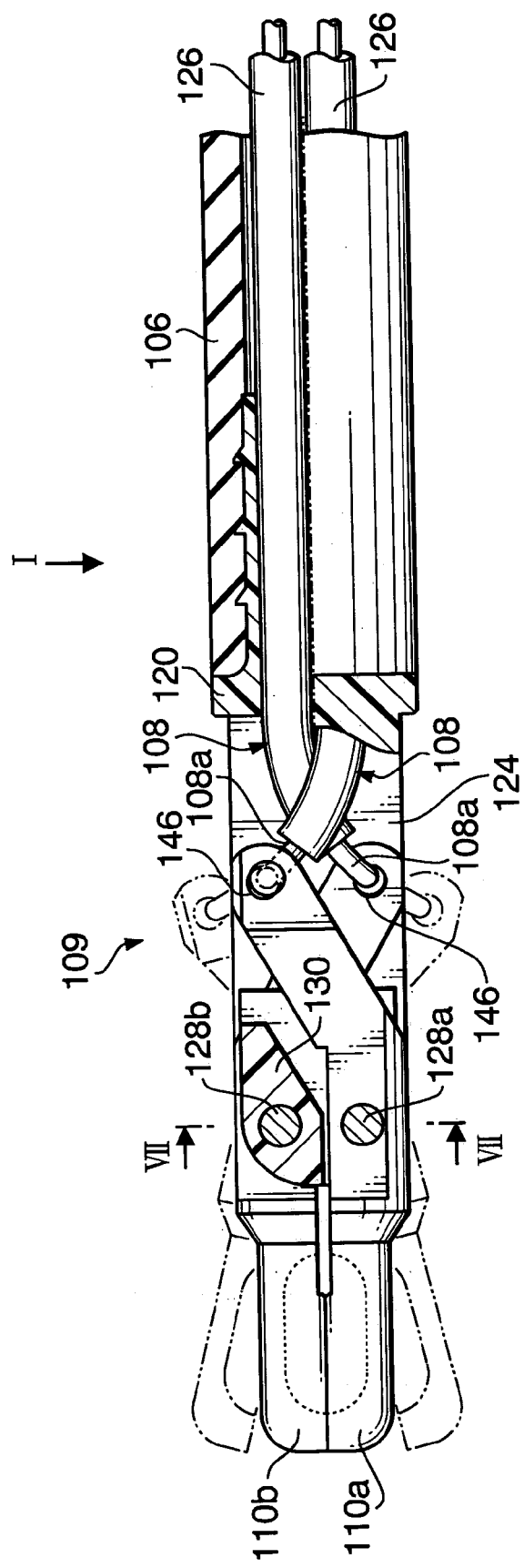
FIG. 3 is partially sectional side view of the distal end of the bipolar high frequency treatment tool shown in FIG. 1.

FIGS. 6A and 6B respectively show a right side view an a rear side view of an insulating block of the bipolar high frequency treatment tool shown in FIG. 1;

FIG. 7 is a sectional view of the electrode assembly taken along the line VII—VII in FIG. 3

Figure 8:
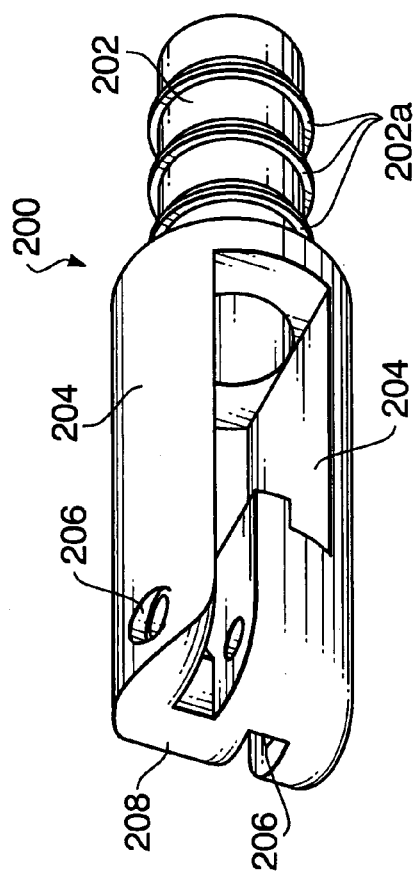
Figure 9:
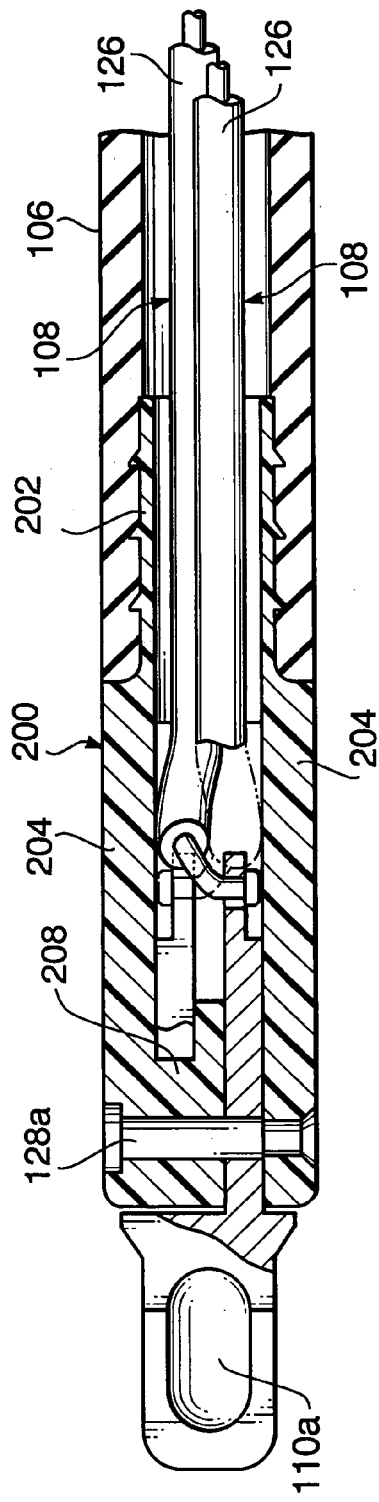

FIG. 8 is a perspective view of a variation of a supporting member of the bipolar high frequency treatment tool shown in FIG. 1; and FIG. 9 is a sectional view of the an end portion of an bipolar high frequency treatment tool according to an embodiment of the invention in which the supporting member shown in FIG. 8 is utilized.

DETAILED DESCRIPTION OF THE EMBODIMENTS

Hereinafter, an embodiment of the invention will be described with reference to the accompanying drawings.

FIG. 1 schematically shows a bipolar high frequency treatment tool 100 according to an embodiment of the invention connected to a high frequency power supply 200.

The treatment tool 100 includes an operation portion 102 and an inserting portion 104 connected to the distal end of the operation portion 102.

The inserting portion 104 is provided in a form and size that allows it to be introduced into a body cavity through a treatment tool inserting channel of an endoscope (not shown). The inserting portion 104 includes an elongated and flexible sheath 106, and a pair of conductive wires 108 (only one is shown) slidably passed through the sheath 106. The sheath 106 is made of insulating material such as poly-tetra-fluoro-ethylene (PTFE). In an exemplary embodiment, the sheath 106 is 1 m to 2 m long and has an outer diameter of 2 mm to 3 mm.

An electrode assembly 109 is mounted to the distal end of the insertion portion 104. The electrode assembly 109 includes first and second electrodes 110a and 110b that are connected to the conductive wires 108.

The operating portion 102 includes a cylindrical portion 112 and a rod portion 114 slidably inserted into the cylindrical portion 112.

The cylindrical portion 112 has a circumferential groove 112a at a proximal end thereof. A user of the treatment tool 100 can hold the operation portion 112 by pinching it at the groove 112a with his index finger and long finger.

The rod portion 114 has a ring 114a into which the user can insert his thumb to slide the rod portion 114 within the cylindrical portion 112 back and forth.

The rod portion 114 is connected with the pair of wires 108 in the cylindrical portion 112 such that the wires 108 retract and proceed in the sheath 106 as the rod portion 114 is moved back and forth with respect to the cylindrical portion 112. It should be noted that the pair of wires 108 may be fixed to each other so that they slide integrally within the sheath 106 to move the pair of electrodes 110 simultaneously.

The conductive wires 108 are detachable connected to power supply lines of the high frequency power supply 200 via a pair of connectors 116 provided to the side surface of the cylindrical portion 112. One of the conductive wires 106 is connected to the positive terminal of the power supply 200 and the other to the negative terminal.

Figure 2:
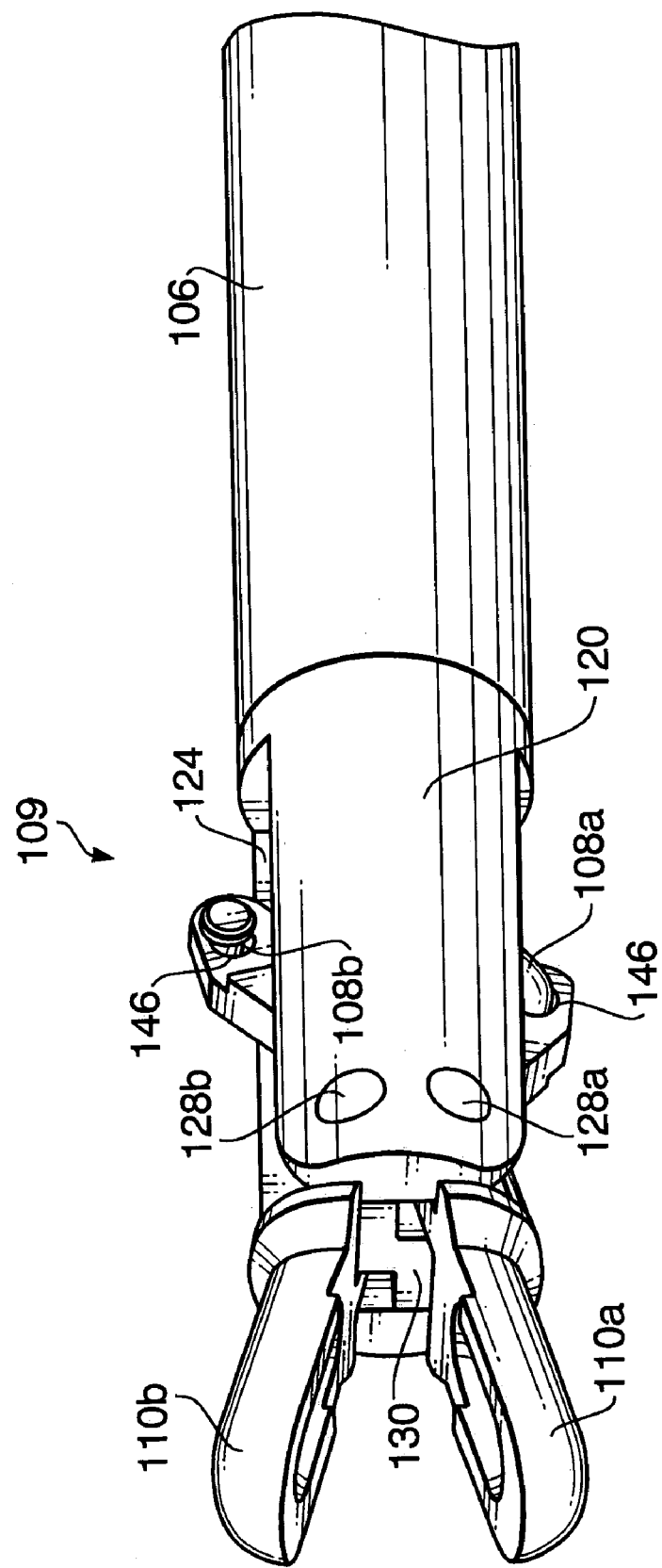
FIG. 2 is a perspective view of the distal end of the bipolar high frequency treatment tool shown in FIG. 1.
Figure 4:
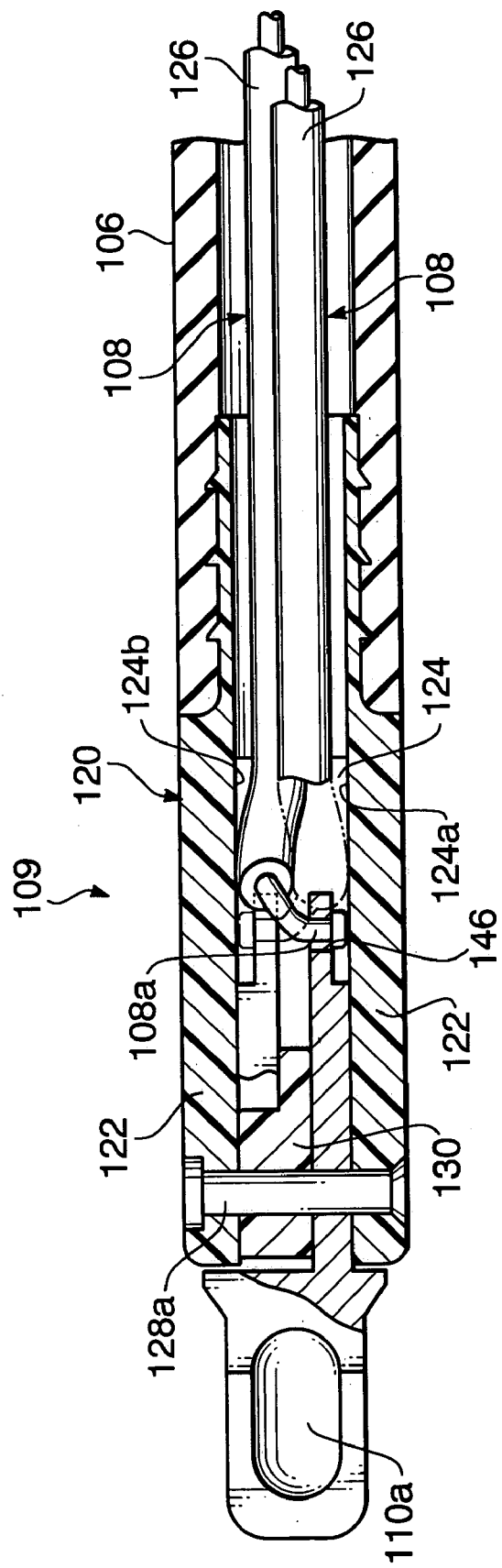
FIG. 4 is a sectional view of the bipolar high frequency treatment tool shown in FIG. 3 observed from the direction indicated by the arrow I.

FIG. 2 is a perspective view of the distal end of the treatment tool 100 shown in FIG. 1. FIG. 3 is partially sectional side view of the distal end of the treatment tool 100 shown in FIG. 1, and FIG. 4 is a sectional view of the treatment tool 100 shown in FIG. 3 observed from the direction indicated by the arrow I. Note that FIGS. 3 and 4 are drawn as a composite view combining cross sectional views at various positions.

The electrode assembly 109 includes a supporting member 120 for pivotably supporting the first and second electrodes 110a and 110b. The supporting member 120 is made of hard insulating material such as rigid plastic and mounted to the distal end of the flexible sheath 106.

As shown in FIG. 4, the supporting member 120 has two arms 122 extending forwards in parallel to each other to form a slit 124 therebetween having a constant width. First and second pins 128a and 128b are supported by the arms 122 in the vicinity of distal end of the arms 122.

The first and second pins 128a and 128b are held parallel to and spaced apart from each other, and perpendicular to first and second inner side surfaces 124a and 124b of the slit 124. The first and second pins 128 are made of stainless steel, for example.

The first and second electrodes 110a and 110b are partially inserted into the slit 124 of the supporting member 120 and pivotably mounted to the first and second pins 128a and 128b. Thus, the electrodes 110a and 110b can move between a closed position as shown in FIG. 3 by solid lines, at which the electrodes 110a and 110b come into contact with each other, and an open position as shown in FIG. 3 by chain double-dashed lines, at which the electrodes 110a and 110b are located apart from each other.

As shown in FIG. 3, the rear ends or proximal ends of the electrodes 110a and 110b are connected with the respective conductive wires 108. Each of the conductive wires 108 is covered with a insulating tube 126 except the end portion 108a thereof at which the conductive wire 108 is connected to the corresponding electrode (110a, 110b).

An insulating block 130 is provided in the slit 124 of the supporting member 120 to prevent the first and second electrodes 110a and 110b from coming into contact to each other within the slit 124. The insulating block 130 is located between the first and second electrodes 110a and 110b and supported by the first and second pins 128a and 128b.

Figure 5:
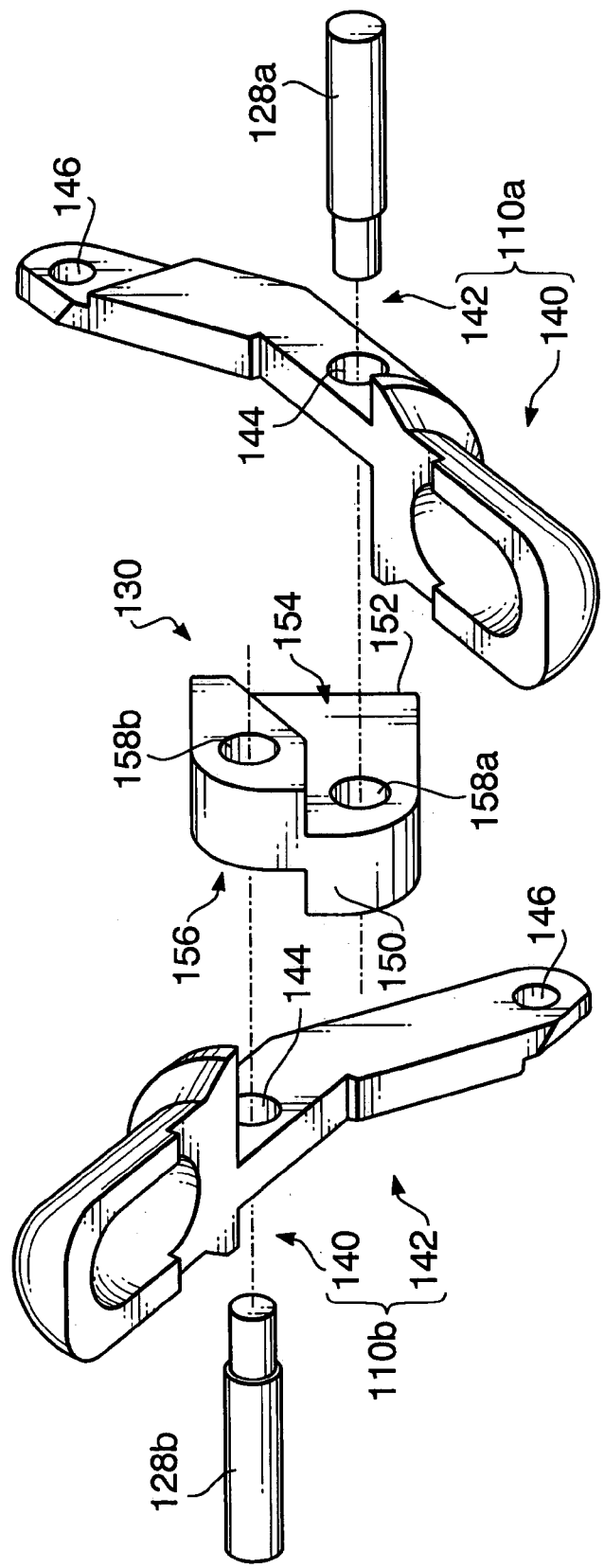
FIG. 5 is an exploded perspective view of a part of an electrode assembly of the bipolar high frequency treatment tool shown in FIG. 1.

FIG. 5 is an exploded perspective view of the electrode assembly 109. Note that the supporting member 120 is not shown in FIG. 5 for clarity of the drawing.

Each of the first and second electrodes 110a and 110b is an elongated member made of conductive metal such as stainless steel. Each electrode (110a, 110b) includes an elongated front (distal) portion 140 and an elongated rear (proximal) portion 142. When the electrodes 110a and 110b are mounted to the supporting member 120, the front portions 140 thereof are located outside of the slit 124 and the back portions 142 thereof are located between the two arms 122.

Two through holes are formed to the back portion 142 of each electrode (110a, 110b). The first one is a supporting hole 144 provided at substantially the center of each electrode (110a, 110b). The other one is a connection hole 146 formed in the vicinity of the rear end of each electrode (110a, 110b).

The first electrode 110a is pivotably mounted to the supporting member 120 by inserting the first pin 128a through the supporting hole 144 thereof, while the second electrode 110b is pivotably mounted to the supporting member 120 by inserting the second pin 128b through the supporting hole 144 thereof.

The tip end of each conductive wire 108, which is exposed from the insulating tube 126, is passed through the connecting hole 146 and thereby connected with the corresponding electrode (110a, 110b).

The rear portion 142 of each electrode (110a, 110b) is slightly bent so that the conductive wires 108 sliding back and forth within the sheath 106 can swing the electrodes 110a and 110b around the respective pins 128a and 128b between the open and closed positions.

The front portion 140 of each electrode (110a, 110b) has a cup like shape. The electrodes 110a and 110b are arranged such that the cup like portions come in contact with each other at the concave sides thereof when the electrodes 110a and 110b are in the closed position.

The insulating block 130 is made of ceramic or resin such as poly-tetra-fluoro-ethylene. The insulating block 130 has front and rear sides (150, 152) and right and left sides (154, 156). The insulating block 130 is located within the slit 124 of the supporting member 120 such that the right and left sides (154, 156) face the right and left inner side surfaces 124a and 124b of the slit 124, respectively.

Two through holes 158a and 158b are formed to the insulating block 130 which are perpendicular to the right and left sides 154 and 156 of the insulating block 130. The insulating block 130 is mounted to the supporting member 120 by inserting the first and second pins 128a and 128b through the first and second through holes 158a and 158b, respectively. Since the insulating block 130 is supported by two pins (128a, 128b), it does not rotate within the slit 124.

It should be noted that the through holes 158a and 158b have inner diameters slightly smaller than the outer diameter of the pins 128a and 128b. Accordingly, the pins 128a and 128b tightly fit into the respective through holes 158a and 158b and thereby prevent the electrode assembly 109 from disassembling.

FIGS. 6A and 6B show the right side 154 and the rear side 156 of the insulating block 130, respectively. Further, FIG. 7 is a sectional view of the electrode assembly 109 taken along the line VII—VII in FIG. 3. The insulating block 130 has substantially the same width W as the slit 124.

The right side 154 of the insulating block 130 is deformed to define a first stepped back surface 154a. Similarly, the left side 156 of the insulating block 130 is deformed to define a second stepped back surface 156a.

As shown in FIG. 7, first and second stepped back surfaces 154a and 154b contribute to form first and second spaces 170a and 170b between the insulating block and the arms 122 of the supporting member 120 for receiving the first and second electrodes, respectively. The first and second stepped back surface 154a and 154b are formed such that the first pin 128a only penetrates the first space 170a and does not expose to the second space 170b, and such that the second pin 128b only penetrates the second space 170b and does not expose to the first space 170a.

The first and second electrodes 110a and 110b are pivotably mounted to the first and second pins 128a and 128b within the first and second spaces 170a and 170b, respectively.

The first and second stepped back surfaces 154a and 156a are formed such that the widths of the first and second spaces 170a and 170b become slightly larger than the widths of the first and second electrode 110a and 110b, respectively.

In the treatment tool 100 configured as above, the first and second electrodes 110a and 110b does not come into contact with each other except when the first and second electrodes 110a and 110b are moved to the closed position since the insulating block 130 is located between the first and second electrode 110a, 110b.

Further, the insulating block 130 supports the first and second pins 128a and 128b passed through the through holes 158a and 158b to prevent the first and second pins 128a from being bent and/or broken by the force exerted thereon from the first and second electrodes 110a and 110b as the first and second electrodes 110a and 110b are moved between the open and closed positions.

Further, since the insulating block 130 has substantially the same width as the slit 124, the arms 122 having the insulating block 130 therebetween do not bend inwardly even if external force is exerted on the arms 122, and hence the arms 122 do not make the first and second electrodes 110a and 110b immovable between the open and closed positions by strongly pressing them.

FIG. 8 is a perspective view of a supporting member 200 which is a variation of the supporting member 120 and can be utilized in the bipolar high frequency treatment tool 100 shown in FIGS. 1 through 7. FIG. 9 is a sectional view of the end portion of the bipolar high frequency treatment tool 100 in which the supporting member 120 is replaced with the supporting member 200.

The supporting member 200 has a base portion 202 that is to be inserted into the flexible sheath 106 of the treatment tool 100. The base portion 202 is formed in a cylindrical shape and is provided with a plurality of circumferential protrusions 202a. The circumferential protrusions 202a dig into the inner surface of the flexible sheath 106 as the base is inserted thereinto and thereby firmly connect the supporting member 200 with the flexible sheath 106. Two arms 204 are extending forwardly from the base to form a slit with a substantially constant width therebetween. Each of the arms 204 are provided with two bores 206 (only one for each arm is shown) at the front end portion through which the pins 128a and 128 can be inserted. An insulating block 208 that has essentially the same form as the insulating block 130 shown in FIG. 5 is integrally formed to the supporting member 200 between the front end portions of the two arms 204.

As described above, the supporting member 200 shown in FIG. 8 has essentially the same configuration as the supporting member 120 of the treatment tool shown in FIGS. 1 through 7 and differs therefrom only in that the insulating block 208 is integrally formed to the arms 204. The supporting member 200 configured as above has higher mechanical strength than the supporting member 120 since the insulating block 208 is integrally formed thereto, and enhance the strength of the electrode assembly 109 against external force. Further, since the supporting member 200 and the insulating block 208 are formed in one component, the electrode assembly 109 can be easily assembled.

The insertion portion 104 of treatment tool 100 configured as above is introduced into a body cavity such as a stomach through an endoscope and the first and second electrodes 110a and 110b are located in the vicinity of a target portion of the mucosa.

Then, the operation portion 102 of the treatment tool 100 is operated such that the pair of conductive wires 108 is slid forwards within the sheath 106 and swing the first and second electrodes 110a and 110b to the open position. Then, the electrodes 110a and 110b are moved by the endoscope such that the target portion of the mucosa is located between the electrodes 110a and 110b.

Next, the pair of conductive wires 108 are retracted by pulling back the rod portion 114 with respect to the cylindrical portion 112 to move the front portions 140 of the electrodes 110a and 110b to the closed position and thereby grasping the target mucosa.

Next, a high frequency electrical power is supplied from the power supply 200 to the first and second electrodes 110a and 110b via the conductive wires 108. As a result, a high frequency current flows through the mucosa placed between the electrodes 110 and coagulates the mucosa.

The present disclosure relates to the subject matter contained in Japanese Patent Application No. P2002-106009, filed on Apr. 9, 2002, which is expressly incorporated herein by reference in its entirety.

What is claimed is:

1. A bipolar high frequency treatment tool having an inserting portion for insertion into a body cavity through an endoscope, comprising:

a supporting member attached to a distal end of said inserting portion, a slit being formed by said supporting member, said slit having first and second inner side surfaces facing each other;

first and second electrodes within said slit of said supporting member and movable between open and closed positions, front portions of said first and second electrodes extending from said slit, said front portions contacting each other in said closed position and being spaced from each other in said open position;

an insulating block having substantially a same width as said slit and being located within said slit between said first and second electrodes, said insulating block having first and second side surfaces facing said first and second inner side surfaces of said slit, respectively, said first and second side surfaces being deformed to define first and second spaces between said insulating block and said first and second inner side surfaces of said slit for receiving said first and second electrodes, respectively; and first and second pins held by said supporting member within said slit parallel to and spaced from each other, wherein said first and second electrodes are pivotably mounted to said first and second pins, wherein said insulating block has first and second through holes extending substantially perpendicularly to said first and second side surfaces of said insulating block, said insulating block being mounted to said supporting member by said first and second pins extending through said first and second through holes, respectively.

2. The bipolar high frequency treatment tool according to claim 1, wherein said first and second spaces have widths slightly larger than the widths of said first and second electrodes, respectively.

3. The bipolar high frequency treatment tool according to claim 1, wherein said insulating block is integral with said supporting member in said slit.

4. An electrode assembly to be mounted to a distal end of an inserting portion of a bipolar high frequency treatment tool, for insertion into a body cavity through an endoscope, said electrode assembly comprising:

a supporting member configured to be attached to a distal end of said inserting portion, a slit being formed by said supporting member, said slit having first and second inner side surfaces facing each other;

first and second electrodes within said slit of said supporting member and movable between open and closed positions, front portions of said first and second electrodes extending from said slit, said front portions contacting each other in said closed position and being spaced from each other in said open position;

an insulating block having substantially a same width as said slit and being located within said slit between said first and second electrodes, said insulating block having first and second side surfaces facing said first and second inner side surfaces of said slit, respectively, said first and second side surfaces being deformed to define first and second spaces between said insulating block and said first and second inner side surfaces of said slit for receiving said first and second electrodes, respectively; and first and second pins held by said supporting member within said slit parallel to and spaced from each other, wherein said first and second electrodes are pivotably mounted to said first and second pins, wherein said insulating block has first and second through holes extending substantially perpendicularly to said first and second side surfaces of said insulating block said insulating block being mounted to said supporting member by said first and second pins extending through said first and second through holes, respectively.

5. The electrode assembly according to claim 4, wherein said first and second spaces have widths slightly larger than the widths of said first and second electrodes, respectively.

6. The electrode assembly according to claim 4, wherein said insulating block is integral with said supporting member in said slit.

* * * * *